United States Patent [19]
Fossel

[11] Patent Number: 5,207,715
[45] Date of Patent: May 4, 1993

[54] METHOD OF DETECTING CANCER BY MEASURING LIPID-PEROXIDATION USING NMR

[75] Inventor: Eric T. Fossel, Chestnut Hill, Mass.

[73] Assignee: The Beth Israel Hospital Association, Boston, Mass.

[21] Appl. No.: 869,052

[22] Filed: Apr. 14, 1992

Related U.S. Application Data

[63] Continuation of Ser. No. 803,775, Dec. 5, 1991, abandoned, which is a continuation of Ser. No. 557,529, Jul. 24, 1990, abandoned.

[51] Int. Cl.$^5$ ............................................. A61B 5/055
[52] U.S. Cl. ................................. 128/653.2; 436/64; 436/71; 436/173
[58] Field of Search ........................ 436/173, 64, 71; 128/653.2

[56] References Cited

U.S. PATENT DOCUMENTS

| | | | |
|---|---|---|---|
| 3,655,700 | 4/1972 | Siddall | 260/405 |
| 4,126,416 | 11/1978 | Sears | 23/230 B |
| 4,226,713 | 10/1980 | Goldberg | 23/230 B |
| 4,472,303 | 9/1984 | Tanihara | 260/112 B |
| 4,933,844 | 6/1990 | Otvos | 364/413.08 |
| 4,940,055 | 7/1990 | Brown | 128/653 A |

OTHER PUBLICATIONS

Science News, "NMR Test Fails To Identify Cancer", vol. 137 p. 236 Apr. 14, 1990.
Shulman, "NMR-Another Cancer-Test Disappointment", The New England Journal of Medicine pp. 1002-1003 vol. 322 No. 14 Apr. 5, 1990.
Bell et al., "'H NMR Studies of human blood plasma," 219, FEB Letters, No. 1, 239-243 (Jul. 1987).
Hessler et al., "Lipoprotein oxidation and . . . ," 3(3), Arteriosclerosis, 215-222 (1983).
Hore et al., "Solvent Suppresion in Fortran . . . ," 55, J. of Mag. Res., 283-300 (1983).
Morel et al., "Low density lipoprotein cytotoxicity . . . ," 24, J. of Lipid Research, 1070 (1983).
Stryer Biochemistry Freeman, New York, 560 (1988).

*Primary Examiner*—Ruth S. Smith
*Attorney, Agent, or Firm*—Lorusso & Loud

[57] ABSTRACT

A technique and an apparatus are disclosed for the detection of cancer using nuclear magnetic resonance (NMR). Specifically, NMR parameters for protons of lipid methyl and/or methylene groups are determined and compared against a corresponding value for healthy patients. Suppression of the water proton signal is employed where necessary in order to obtain a suitable spectrum for the non-water component protons. In the event that a positive reading is obtained, the level of plasma triglycerides is determined and if it is high, the patient's bodily fluid sample is further subjected to second proton nuclear magnetic spectroscopy. The area or the intensity of the portion correlating to 2.0 and 2.8 ppm of the resonance line generated in the second NMR is measured which discriminates between true and false positive results from the proton NMR reading and determines the presence or absence of cancer in the patient.

59 Claims, 4 Drawing Sheets

5,207,715

METHOD OF DETECTING CANCER BY MEASURING LIPID-PEROXIDATION USING NMR

This is a continuation of copending application Ser. No. 07/803,775 filed on Dec. 5, 1991 now abandoned which is a continuation of U.S. Ser. No. 07/557,529 filed Jul. 24, 1990 now abandoned.

BACKGROUND OF THE INVENTION

1. Field of the Invention

The present invention relates to a diagnostic method and apparatus for the detection of cancer in a living patient.

2. Prior Art

Attempts utilizing the technique of nuclear magnetic resonance (NMR) to aid in arriving at a clinical diagnosis of cancer are well known in the prior art.

Damadian was the first to propose any medical use for nuclear magnetic resonance (NMR) and that was for the detection of malignancy in tissue. See R. Damadian, "Tumor Detection by Nuclear Magnetic Resonance," *Science* 171:1151–1153 (1971). U.S. Pat. No. 3,789,832 issued to Damadian covers an apparatus and method for application of nuclear magnetic resonance to surgically removed specimens to measure $T_1$ and $T_2$ for proton relaxation times, which values, compared against values for healthy tissue, were taken as an indication of cancer. U.S. Pat. Nos. 4,411,270 and 4,354,499 issued to Damadian cover apparatus and method for cancer detection with NMR imaging and scanning of whole-body specimens.

A number of other investigators also reported that nuclear magnetic resonance relaxation times ($T_1$) for water protons in organs of tumor bearing animals have higher values than the corresponding $T_1$ for water structure in organs of healthy animals. See Frey et al, *J. Natl. Cancer Inst.* 49, 903 (1972); Inch et al, *J. Natl. Cancer Inst.* 52, 353 (1974); Iijima et al, *Physiol. Chem. and Physics* 5, 431 (1973); and Hazlewood et al, *J. Natl. Cancer Inst.* 52, 1849 (1974).

Today, despite uncertainty regarding mechanistic details, it is well known that biophysical changes which occur in malignant cells often result in alterations of the proton NMR signal. See D.G. Taylor et al, "A Review of the Magnetic Resonance Response of Biological Tissue and Its Applicability to the Diagnosis of Cancer by NMR Radiology," *Computed Tomography*, 5:122–133 (1981). Such changes form the physical basis for detection of tumors by proton NMR imaging. See R. Zimmerman et al, "Cerebral NMR: Diagnostic Evaluation of Brain Tumors by Partial Saturation Technique with Resistive NMR, *Neuroradiology* 27:9–15 (1985) and K. Ohtomo, " Hepatic Tumors: Differentiation by Transverse Relaxation Time ($T_2$) of Magnetic Resonance Imaging, *Radiology* 155:421–423 (1985). However, NMR imaging is not likely to be widely applied as a screening test for malignancy because of accessibility and economic factors.

Proton NMR studies on excised tumors, as well as on plasma and serum, from experimental animals and patients have often shown differences in the relaxation parameters $T_1$, $T_2$ and $T_2^*$, $T_2^*$ being a combination of $T_2$ from intrinsic relaxation and relaxation induced by magnetic field inhomogeneities, as a function of malignancy. Such findings have been reported by the following:

L. McLachlan, "Cancer-induced Decreases in Human Plasma Proton NMR Relaxation Rates." *Phys. Med. Biol.* 25:309–315 (1980):

F. Smith et al, "Nuclear Magnetic Resonance Imaging of the Pancreas," *Radiology* 142:677–680 (1982);

P. Beall et al, "The Systemic Effect of Elevated Tissue and Serum Relaxation Times for Water in Animals and Humans with Cancers," *NMR Basic Principles and Progress*, P. Diehl et al, Eds., 19:39–57 (1981);

R. Floyd, "Time Course of Tissue Water Proton Spinlattice Relaxation in Mice Developing Ascites Tumor," *Cancer Res.* 34:89–91 (1974);

C. Hazlewood et al, "Relationship Between Hydration and Proton Nuclear Magnetic Resonance Relaxation Times in Tissues of Tumor Bearing and Nontumor Bearing Mice: Implications for Cancer Detection," *J. Natl. Cancer Inst.* 52:1849–1853 (1974); and R. Klimek et al, "A Discussion of Nuclear Magnetic Resonance (NMR) Relaxation Time of Tumors in Terms of Their Interpretation as Self-organizing Dissipative Structures, and of Their Study of NMR Zeugmatographic Imaging," *Ginekol Pol.* 52:493–502 (1981).

However, due to extensive overlap of groups and small differences between the means of groups, these methodologies are not clinically useful.

While most of the prior art mentioned above describes applications of NMR to analysis of tissue, it is also known to subject bodily fluids to such analysis. This is described, for example, by Beall et al., supra.

The foregoing prior art studies and methods rely on the observation of the composite NMR signal arising from all protons in the tissue or blood derived samples. This composite signal is dominated by the protons of water, obscuring the NMR signal from other proton-Containing constituents of the sample. Indeed, the prior art believed that the apparent correlation between malignancy and observed changes in NMR parameters was due to "changes in water structure," quoting Frey et al., supra.

In other applications of proton NMR spectroscopy, it was known to suppress the signal from the solvent (such as water), in a sample.

It was discovered that the components of the NMR spectrum which have significant predictive value may be masked by other materials in the sample. By eliminating the masking, as by eliminating the water signal, the previously masked spectrum of these components was revealed. In U.S. Pat. No. 4,912,050 entitled "Process for the Screening of Cancer Using Nuclear Magnetic Resonance," issued to Eric T. Fossel on Mar. 27, 1990, those discoveries were incorporated into a reliable method of diagnosing the presence of cancer in a living patient. In accordance with that invention, a sample of a patient's bodily fluid is subjected to nuclear magnetic resonance spectroscopy to generate a nuclear magnetic resonance spectrum. A resonance line generated by a non-water component of the sample is selected, and the full width of this resonance line, e.g., at half its height, is measured. The full width so measured has proved to be a statistically reliable measure of the presence or absence of cancer in the patient.

The above described test of water-suppressed proton NMR of plasma discriminates between persons with untreated cancers and others with better than 90% accuracy. No prior non-invasive test for cancer had reached even close to that level of accuracy. False positive results, however, have been obtained. In accordance to a later invention, U.S. Pat. No. 4,918,021 ('021) entitled "Process for the Detection of Cancer" issued to Eric T. Fossel on Apr. 17, 1990, it has been discerned that the major source of false positive results are those persons with high levels of plasma triglycerides. Thus, in accordance with the '021 patent, a method and apparatus was developed to improve upon the accuracy of a non-invasive method to determine the presence of cancer in a living patient using C-13 NMR.

In the past in accordance with the teachings of the '021 patent, in the event that a positive readinq is obtained in accordance with the present invention, the level of triglycerides is determined. If the level of triglycerides is high, then the patient's bodily fluid is further subjected to C-13 nuclear magnetic resonance spectroscopy. The resonance spectrum of the plasma C-13 spectra discriminates between true and false positive results to determine the presence or absence of cancer in the patient with a higher degree of accuracy than was previously possible. C-13 NMR looks at the ratio of fatty acids with a single double bond versus fatty acids with two double bonds. However, C-13 is costly and takes a relatively long time to run.

The present invention is an improved method for screening for the presence of cancer which would eliminate the need to use C-13 to screen for false positives as disclosed in the '021 patent. The advantage to the present invention is the relatively short time to run the test and the relative decrease in cost.

These and other objects and features of the present invention will become apparent to those skilled in the art from a reading of the description of the invention, taken together with the drawing, which follow.

SUMMARY OF THE INVENTION

Accordingly, the principal object of the present invention is to provide a method of confirming a diagnosis by NMR water suppressed proton method of the presence of cancer in a living patient.

Another object of the present invention is to provide a method to differentiate between true and false positive results obtained in a water suppressed proton NMR test in diagnosing the presence of cancer in a living patient.

Yet another object of the invention is to provide a method for detecting the presence of cancer in a patient which can be carried out on a sample of the patient's body fluid.

A further object of the present invention is to provide a method of diagnosing the presence of cancer in a living patient which is more accurate than previously known methods.

In accordance with the present invention, a sample of a patient's bodily fluid is subjected to proton nuclear magnetic resonance spectroscopy to generate a nuclear magnetic resonance spectrum. A resonance line generated by a non-water component of the sample is selected, and the area under the peak of the resonance line or the intensity of the peak is measured. The area or intensity so measured, as compared to a standard control, provides a statistically reliable indication of the presence or absence of cancer in the patient.

Normally the ratio of H-1 resonances at 2.0 ppm (allylic) to those at 2.8 ppm (bis-allylic) is between 2.0 and 2.5. This arises since in normal persons the ratio of polyunsaturated fatty acids to monounsaturated fatty acids is more than 9:1.

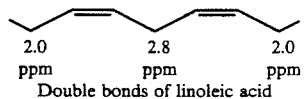
Double bonds of linoleic acid

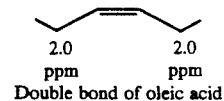
Double bond of oleic acid

The most abundant polyunsaturated fatty acid in plasma lipoproteins is linoleic acid and the most abundant monounsaturated fatty acid is oleic acid. In a cancer patients where peroxidation of lipids occurs there will be a decrease of linoleic and other polyunsaturated fatty acids relative to monosaturated fatty acids because they are more reactive with free radicals than monosaturated fatty acids. This results in a decrease in the resonance at 2.8 ppm and an increase in the ratio of the 2.0 ppm/2.8 ppm resonances. Ratios elevated above 2.5 indicate the presence of cancer. The resonance at 2.0 and 2.8 ppm are illustrated in the spectrum in FIG. 2.

In preferred embodiments, the bodily fluid is blood, spinal fluid, or bone marrow plasma; although blood plasma or serum is especially advantageous. False positive results in the initial proton NMR spectra due to hypertriglyceridemia can be distinguished in the resulting spectra of peroxidized lipoproteins by measuring the ratio of peroxidized lipoproteins and comparing to a standard.

DESCRIPTION OF THE PREFERRED EMBODIMENTS

Figure 1:
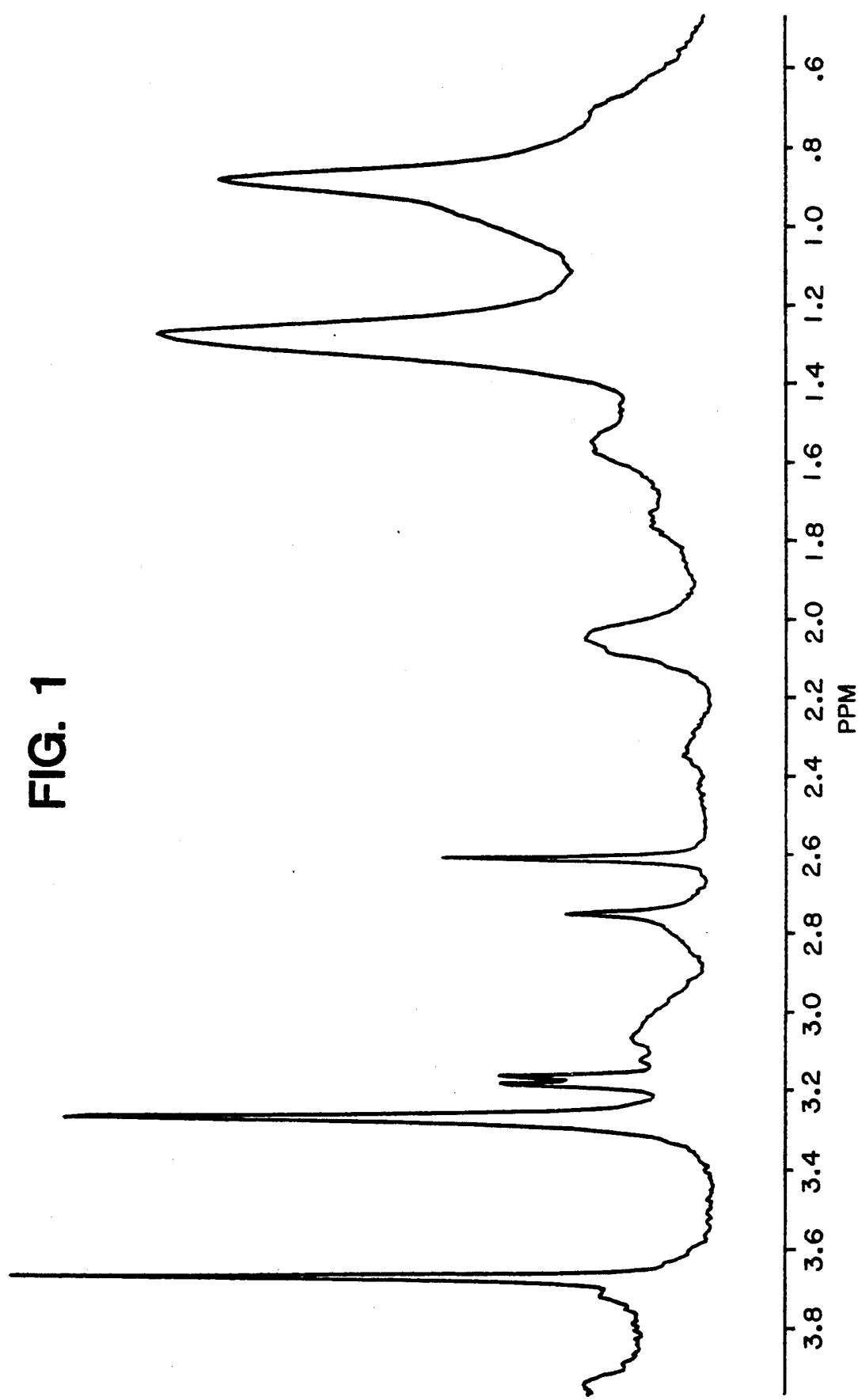
FIG. 1 is a typical 360 MHz NMR spectrum for the non-water components (water-suppressed) of a plasma sample from a healthy control obtained in accordance with the present invention.

At the outset the invention is described in its broadest overall aspects with a more detailed description following. The present invention is a method to detect the presence of cancer in a living patient. In accordance with the invention, a sample of a patient's bodily fluid is subjected to proton nuclear magnetic resonance spectroscopy to generate a nuclear magnetic resonance spectrum. Since components of the NMR spectrum which have significant predictive value may be masked by other materials in the sample, the masking is eliminated to produce the NMR spectrum. A resonance line generated by a non-water component of the sample is selected, and the full width of this resonance line, e.g., at half its height, is measured to provide a reliable measure of the presence or absence of cancer in the patient. The above procedure is described in '050 Fossel patent, the teachings of which are incorporated herein by reference.

In the event that a positive reading is obtained, this reading may indicate the presence of cancer in the patient, or it may be a false positive reading. It has been discovered that a major source of false positive readings are persons with high levels of plasma triglycerides.

Accordingly, in order to differentiate between true and false positive readings. the sample tested previously is subjected to a second proton NMR spectroscopy for those who have elevated triglyceride levels. The false positive results due to hypertriglyceridemia and, conversely, the presence of cancer in the patient, can be reliably determined from the resulting ratios of peroxidized lipoproteins as found in the resulting spectra as compared to a standard.

In one important embodiment of this invention, proton NMR spectroscopy is performed initially on the sample to be tested. The water suppressed proton NMR spectrum obtained on human blood plasma is dominated by the resonances of the plasma lipoprotein lipids. As taught in accordance with '050 Fossel patent, without water suppression, these non-water resonances are virtually overwhelmed by the water. Signal averaging allows observation of resonances of some moieties associated with non-water bodily fluid components, at high magnetic fields, even in the presence of the water resonance. However, the capability of modern NMR spectrometers to suppress nearly completely the water proton resonance will facilitate this reading. The water suppressed proton NMR spectrum of plasma is essentially that of plasma lipoproteins and a few low molecular weight molecules.

The process of the present invention operates on any lipid-containing bodily fluid, blood, or bone marrow plasma. Plasma, whole blood, or serum may be used. While the test may be performed on any such lipid-containing body fluid, work to date has focused on blood plasma. In blood the lipids, inclusive of cholesterol, triglycerides and phospholipids, are present in the form of lipoproteins. The test for cancer will typically be performed in vitro, preferably on serum or plasma.

The selected fluid of a suspect patient or other person to be screened for cancer is exposed to a magnetic field and radio-frequency energy to generate a nuclear magnetic resonance signal which is then processed to obtain a value for the selected parameter, e.g., $W_{\frac{1}{2}}$, for lipid methyl and/or methylene protons. A relatively broad range of proton frequencies may be employed, e.g., 60 MHz and higher; 360 MHz or above is a preferred frequency. If cost is not a factor, 500 MHz may be the preferred frequency.

Figure 2:
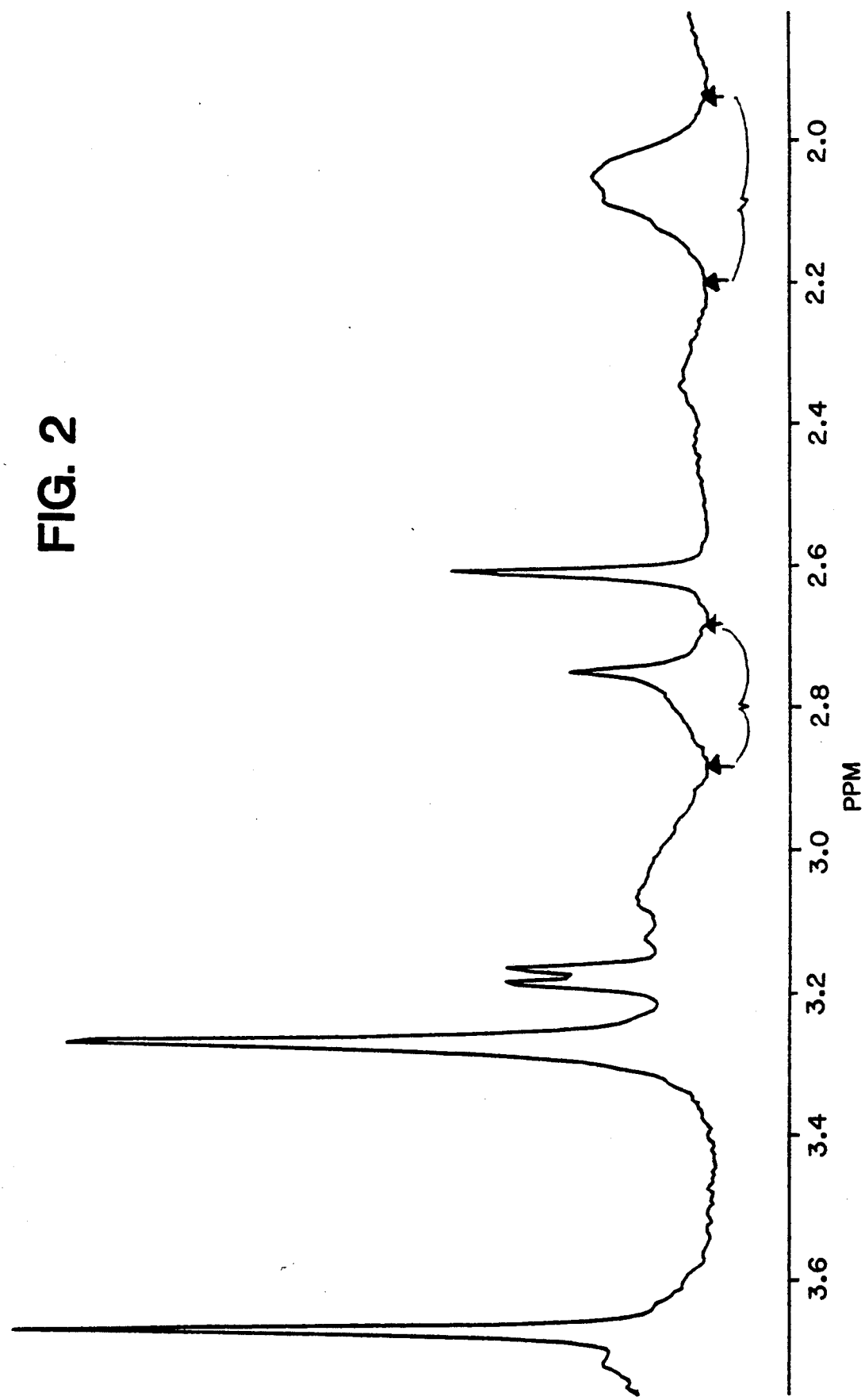
FIG. 2 is an expanded view of the reading of the sample of FIG. 1 showing of the region of the spectra containing resonances at 2.0 and 2.8 ppm.
Figure 4:
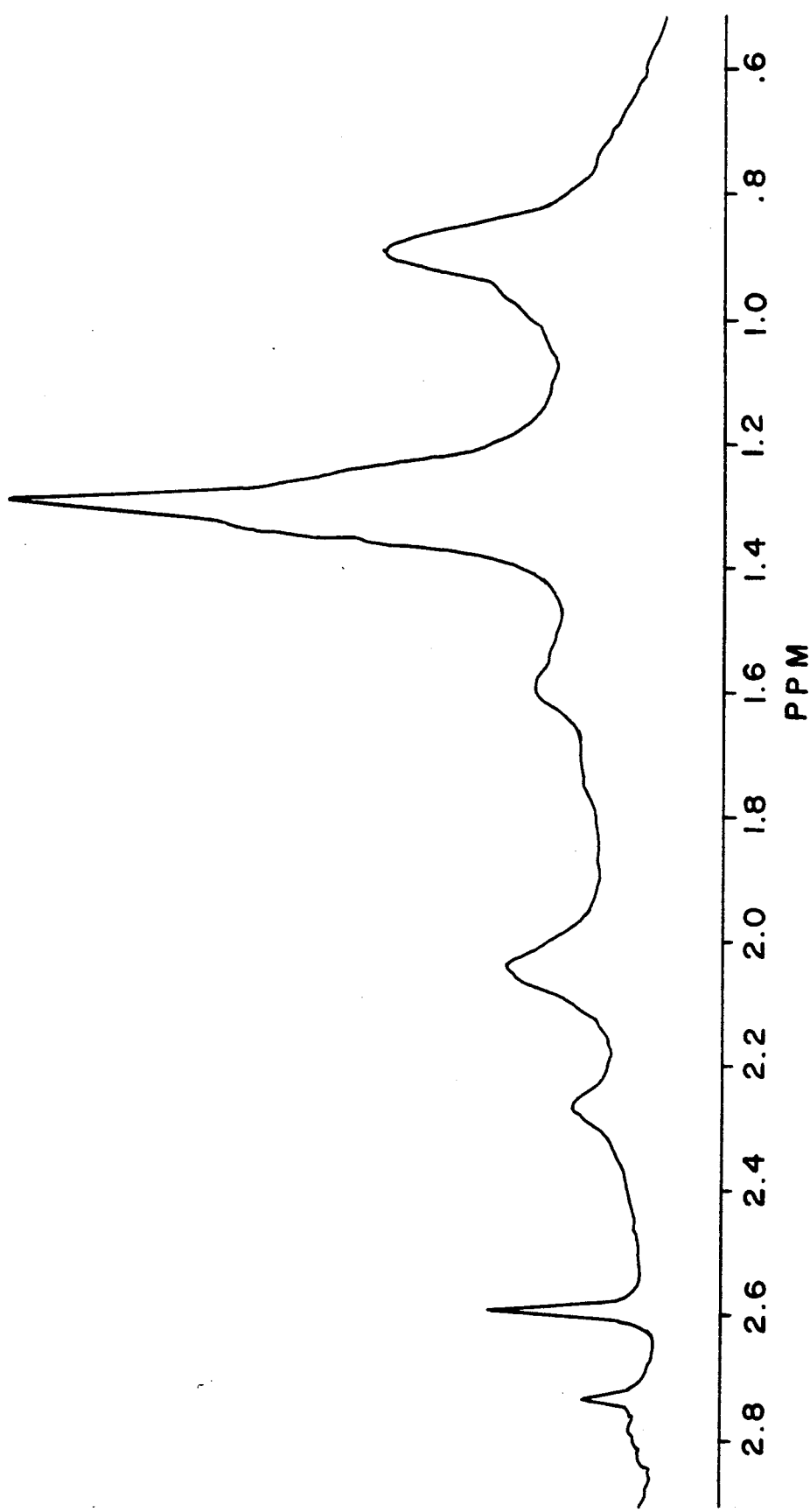
FIG. 4 is a 360 MHz NMR spectrum for the non-water components (water-suppressed) of a plasma sample from a cancer patient showing an expanded view of the reading of the sample and the region of the spectra containing resonances at 2.0 and 2.8 ppm.

FIG. 1 shows a water suppressed proton spectrum of a healthy control, and FIG. 2 shows an expanded spectrum of the same sample showing the region from 2.0 to 2.8 ppm (parts per million of resonance frequency). FIG. 4 shows a water suppressed proton spectrum of a cancer patient showing an expanded view of the reading of the sample and the region of the spectra containing resonances at 2.0 and 2.8 ppm. The resonances in the region from 2.0 to 2.8 ppm arise from the fatty acid groups of the lipoprotein lipids. Accordingly, in its preferred embodiments, the present invention uses one of a number of conventional water suppression techniques, i.e., techniques for suppression of the water proton NMR signal. Numerous techniques have been devised to suppress the water proton NMR signal in other contexts. These techniques have been set out in the '050 Fossel patent.

In accordance with the teachings in the '050 Fossel patent, the linewidth at half-height of the resonances of moieties, e.g., methyl and methylene groups, associated with the lipids of plasma lipoproteins are treated as the variable of interest. Full width at half-height $W_{\frac{1}{2}}$(linewidth) of an NMR resonance line is inversely proportional to the apparent spin-spin relaxation time $(T_2^*)$, i.e. $W_{\frac{1}{2}} =$ $$\frac{1}{\pi T_2^*}$$

The detected value for the selected parameter is then compared with the corresponding parameter for the healthy controls. In a preferred embodiment, values for methyl and methylene are averaged and an average value of 33 Hz or less at a proton frequency of 360 MHz (8.45T) or 400 MHz (9.40 T) is taken as an indication of malignancy.

If a positive reading is obtained from the water suppressed proton NMR spectrum of a plasma sample from a patient, a second level of testing to confirm the diagnosis is performed. First, a conventional test, commonly called a triglyceride analysis, is performed to determine the triglyceride level of the patient. If the triglyceride level is normal, the positive reading from the water-suppressed proton NMR spectroscopy is a true positive and indicates the presence of cancer in the patient. If the triglyceride level is above normal, in order to differentiate between true and false positive results, a second proton NMR spectra on the plasma sample already obtained from the patient is conducted.

False positive results due to hypertriglyceridemia can be reliably distinguished from true positive results by substantial differences in ratio of oxidized lipoproteins in the resulting spectra. Accordingly, the plasma sample already obtained from the suspect patient to be screened is exposed to a magnetic field and radio frequency energy to generate a nuclear magnetic signal which is then processed to obtain a second proton NMR value.

It is possible, as with C-13 NMR as practiced in the '021 Fossel patent, that spectroscopy according to the method of the instant invention can be performed initially on a patient as a method to diagnose the presence of cancer, without first performing a proton NMR spectroscopy as described above. This has not yet been tested, however.

Any conventional modern NMR spectrometer may be used in the practice of the present invention. In the preferred embodiments, an NMR spectrometer with a magnet at constant field strength is used and the NMR signal is Fourier transformed, with the full linewidth at half-height for proton resonances of methyl and methylene groups, and then proton NMR resonances of lipoproteins at 2.0 and 2.8 ppm which are the NMR parameters of interest.

As noted in the '050 Fossel patent, correct sample preparation and execution is essential to carry out a successful measurement on plasma. Blood is collected in tubes containing 70 l of a solution of 15% $Na_2$ EDTA. Blood was maintained at 4° C. until centrifugation. Plasma was separated and stored at 4° C. until NMR analysis. Plasma samples were never frozen because freezing destroys lipoprotein lipid structural integrity.

Samples which showed any visible sign of hemolysis were excluded.

In the preferred embodiment, spectra were obtained at 20°-22° C. at magnetic field strengths of 360 MHz or greater. Other tests were conducted successfully at temperatures of 30° C. and 37° C. The samples were shimmed individually on the area of the proton free induction decay until the full width at half height of the water resonance was 4Hz or less. Of course, careful shimming is an assumed component of good NMR laboratory technique. Of course, the field strength used will determine the length of time in which a sample is taken. In addition, to the experimental conditions, accurate results require careful review of a patient's medical record to arrive at the patient classification.

In accordance with the '050 Fossel patent, the spectrometer contains means for selecting at least one and preferably a plurality such as two NMR resonance lines in the NMR spectrum of the sample and, in the first step of the present invention, measuring the line width of the line or lines so selected. Preferably, the linewidth is measured at half the height of the line, but this is not necessary and linewidth can be measured at any predetermined fraction of the height of the line in question. Measurement at half of line height is preferred because this is a standard measurement carried out in the field of NMR spectroscopy. The spectrometer also contains means for measuring selected peaks, useful for the examination of the second proton NMR spectra. The spectrometer also is of conventional construction and includes in addition to all its other structure a means for storing a value or range of values. In the preferred embodiment, an area or intensity which is either measured directly or derived from a plurality of such direct measurements is compared with a value or range of values which represents the value or range of values to be expected from normal patients, i.e. patients who are free of cancer. In accordance with the invention, the spectrometer also includes means for classifying the measured or derived areas of the 2.0 or 2.8 ppm resonances or intensities of the 2.0 or 2.8 ppm and number of peaks as normal (i.e. cancer-free) or abnormal (i.e. cancerous) based upon the stored information. This may be done by comparison, subtraction, or any other appropriate mathematical operation.

In the preferred embodiment, the selecting and measuring means is pre-adjusted to measure the areas or intensities of the 2.0 ppm and 2.8 ppm resonances of the peroxidized lipoproteins in the spectra. This may include suppressing the signal of water from the NMR spectrum of the sample, or may alternatively be done directly where the spectrometer is sensitive enough to do so.

EXAMPLE

Figure 3:
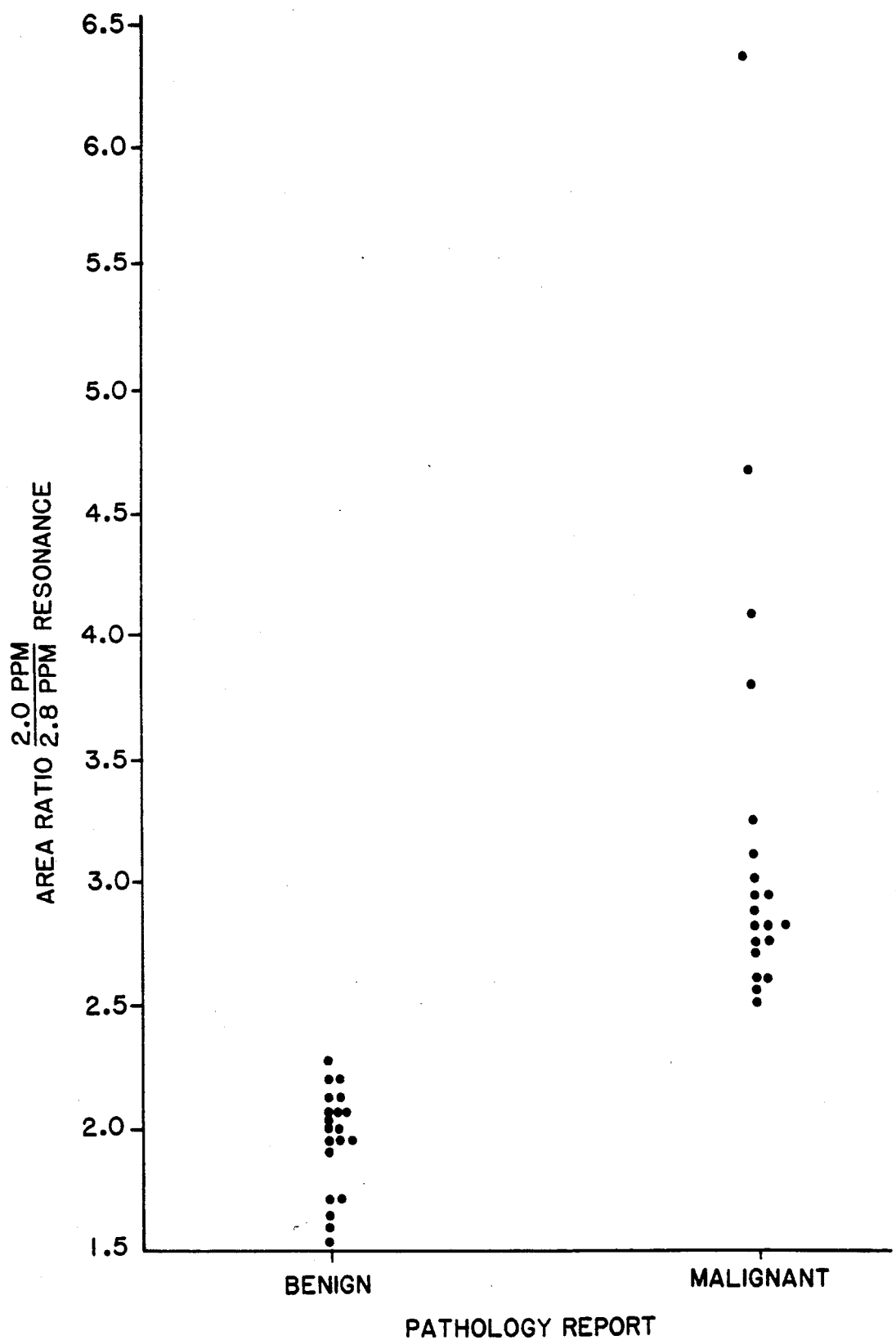
FIG. 3 shows the results of a study performed using the method of the present invention.

In this example, the method of the present invention was applied to a group of 40 patients. The samples were tested in accordance with the method of the instant invention. The results as show in FIG. 3 show the clustering of those samples indicating malignancy. The area of the resonance lines generated according to the method of the instant invention were measured. The results show that the ratio of the samples tested (2.0 ppm to 2.8 ppm) is an indicator of the presence of cancer.

The invention may be embodied in other specified forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range or equivalency of the claims are therefore intended to be embraced therein.

What is claimed is:

1. A method of diagnosing the presence of cancer in a living patient, comprising the following steps:
   a) subjecting a blood component sample from a patient to be tested to proton nuclear magnetic resonance spectroscopy to generate a NMR spectrum from which undesirable signals have been suppressed;
   b) selecting a lipoprotein resonance line for lipid peaks in said spectrum;
   c) measuring the full width at half-height of said resonance line;
   d) classifying the full width measured into either a category of normal full widths or into a category of abnormal full widths as compared to a predetermined standard for which abnormal full widths indicate the presence of cancer;
   e) for measured full width readings classified as abnormal in step d), measuring the triglyceride level of the blood component sample;
   f) classifying the triglyceride level so measured into the category of normal levels or above normal levels;
   g) for component samples having above normal levels of triglycerides, subjecting the blood component sample to a second proton nuclear magnetic resonance spectroscopy to generate an NMR spectrum;
   h) selecting a resonance line for lipoproteins in the region in said spectrum;
   i) measuring the area of said resonance line;
   j) classifying the NMR spectrum into a category of normal spectrum or into a category of abnormal spectrum as compared to a predetermined standard for which abnormal spectrum indicate the presence of cancer.

2. The method of claim 1, wherein said subjecting step
   a) includes suppressing the water signal.

3. The method of claim 1, wherein said subjecting step
   a) comprises obtaining a blood sample from the patient, removing red cells therefrom, and subjecting the plasma in the blood sample to nuclear magnetic resonance spectroscopy.

4. The method of claim 1, wherein the proton resonance is above 60 MHz.

5. The method of claim 4, wherein the proton resonance is equal to or above 360 MHz.

6. The method of claim 1 wherein the ratio of the areas of the peaks of the second proton NMR spectra at 2.0 ppm and 2.8 ppm is indicative of the presence of cancer.

7. A method of diagnosing the presence of cancer in a living patient, comprising the following steps:
   a) subjecting a blood component sample from a patient to be tested to proton nuclear magnetic resonance spectroscopy to generate a NMR spectrum from which undesirable signals have been suppressed;
   b) selecting a lipoprotein resonance line for lipid peaks in said spectrum;

c) measuring the full width at half height of said resonance line;

d) classifying the full width measured into either a category of normal full widths or into a category of abnormal full widths as compared to a predetermined standard for which abnormal full widths indicate the presence of cancer;

e) for measured full width readings classified as abnormal in step d), measuring the triglyceride level of the blood component sample;

f) classifying the triglyceride level so measured into the category of normal levels or above normal levels;

g) for component samples having above normal levels of triglycerides, subjecting the blood component sample to a second proton nuclear magnetic resonance spectroscopy to generate an NMR spectrum;

h) selecting a resonance line for lipoproteins in the region in said spectrum;

i) measuring the intensity of said resonance line; and j) classifying the NMR spectrum into a category of normal spectrum or into a category of abnormal spectrum as compared to a predetermined standard for which abnormal spectrum indicate the presence of cancer.

8. The method of claim 7, wherein said subjecting step
a) includes suppressing the water signal.

9. The method of claim 7, wherein said subjecting step
a) comprises obtaining a blood sample from the patient, removing red cells therefrom, and subjecting the plasma in the blood sample to nuclear magnetic resonance spectroscopy.

10. The method of claim 7, wherein the proton resonance is above 60 MHz.

11. The method of claim 7, wherein the proton resonance is equal to or above 360 MHz.

12. The method of claim 7 wherein the ratio of the intensities of the peaks of the second proton NMR spectra at 2.0 ppm and 2/8 ppm is indicative of the presence of cancer.

13. A method of diagnosing the presence of cancer in a living patient, comprising the following steps:
a) subjecting a blood component sample from a patient to be tested to nuclear magnetic resonance spectroscopy to generate an NMR spectrum from which undesirable signals have been suppressed;
b) selecting a plurality of lipoprotein resonance lines from lipid peaks in said spectrum;
c) measuring the full width at half-height of each of said resonance lines;
d) deriving from all full widths so measured a composite linewidth;
e) classifying the composite linewidth derived into a category of normal composite linewidths or into a category of abnormal composite linewidths as compared to a predetermined standard for which abnormal composite linewidths indicate the presence of cancer;
f) for measured composite linewidths classified as abnormal composite linewidths, measuring the triglyceride levels of the blood component sample;
g) classifying the triglyceride level so measured into the category of normal levels or above normal levels;
h) for blood component samples having above normal levels of triglycerides, subjecting the blood component sample to a second proton nuclear magnetic resonance spectroscopy to generate an NMR spectrum;
i) selecting a plurality of resonance lines for lipoproteins in the region in said spectrum;
j) measuring the average areas for each of said resonance lines line; and
k) classifying the second proton NMR spectrum into a category of normal or into a category of abnormal as compared to a predetermined standard for which abnormal spectrum indicate the presence of cancer.

14. The method of claim 13 wherein said, deriving step comprises the step of computing the ratio of the average of the 2.0 ppm/2.8 ppm areas of the resonance lines.

15. The method of claim 13 wherein said plurality is two.

16. The method of claim 13 wherein the ratio of the areas of the peaks of the second proton NMR spectra at 2.0 and 2.8 ppm is indicative of the presence of cancer.

17. A method of diagnosing the presence of cancer in a living patient, comprising the following steps:
a) subjecting a blood component sample from a patient to be tested to nuclear magnetic resonance spectroscopy to generate an NMR spectrum from which undesirable signals have been suppressed;
b) selecting a plurality of lipoprotein resonance lines from lipid peaks in said spectrum;
c) measuring the full width at half-height of each of said resonance lines;
d) deriving from all full widths so measured a composite linewidth;
e) classifying the composite linewidth derived into a category of normal composite linewidths or into a category of abnormal composite linewidths as compared to a predetermined standard for which abnormal composite linewidths indicate the presence of cancer;
f) for measured composite linewidths classified as abnormal composite linewidths, measuring the triglyceride levels of the blood component sample;
g) classifying the triglyceride level so measured into the category of normal levels or above normal levels;
h) for blood component samples having above normal levels of triglycerides, subjecting the blood component sample to a second proton nuclear magnetic resonance spectroscopy to generate an NMR spectrum;
i) selecting a plurality of resonance lines for lipoproteins in the region in said spectrum;
j) measuring the intensity for each of said resonance lines; and
k) classifying the second proton NMR spectrum into a category of normal or into a category of abnormal as compared to a predetermined standard for which abnormal spectrum indicate the presence of cancer.

18. The method of claim 17 wherein said deriving step comprises the step of computing the ratio of the average of the 2.0 ppm/2.8 ppm areas of the resonance lines.

19. The method of claim 17 wherein said plurality is two.

20. The method of claim 17 wherein the ratio of the intensities of the peaks of the second proton NMR spectra at 2.0 and 2.8 ppm is indicative of the presence of cancer.

21. A method of diagnosing the presence of cancer in a living patient, comprising the following steps:
 a) subjecting a sample from a patient to be tested to nuclear magnetic resonance spectroscopy to generate an NMR spectrum;
 b) selecting an NMR resonance line in said spectrum from a non-water component of said sample;
 c) measuring the full width at half-height of said resonance line;
 d) classifying the full width measured into either a category of normal full widths or into a category of abnormal full widths as compared to a predetermined standard for which abnormal full widths indicate the presence of cancer;
 e) for measured full widths classified as abnormal full widths, measuring the triglyceride levels of the sample;
 f) classifying the triglyceride level so measured into the category of normal levels or above normal levels;
 g) for samples having above normal levels of triglycerides, subjecting the sample to a second nuclear magnetic resonance spectroscopy to generate an NMR spectrum;
 h) selecting a resonance line for lipoproteins in the region in said spectrum;
 i) measuring the area of said resonance line; and
 j) classifying the NMR spectrum into a category of normal spectrum or into a category of abnormal spectrum as compared to a predetermined standard for which abnormal spectrum indicate the presence of cancer.

22. The method of claim 21 wherein the non-water component is a lipid.

23. The method of claim 21 wherein the sample is blood plasma, spinal fluid or bone marrow plasma, and wherein said selected resonance line is from the allylic and/or bis-allylic groups of the lipoprotein lipids.

24. The method of claim 21 wherein the ratio of the area of the peaks of the second proton NMR spectrum at 2.0 and 2.8 ppm is indicative of the presence of cancer.

25. A method of diagnosing the presence of cancer in a living patient, comprising the following steps
 a) subjecting a sample from a patient to be tested to nuclear magnetic resonance spectroscopy to generate an NMR spectrum;
 b) selecting an NMR resonance line in said spectrum from a non-water component of said sample;
 c) measuring the full width at half-height of said resonance line:
 d) classifying the full width measured into either a category of normal full widths or into a category of abnormal full widths as compared to a predetermined standard for which abnormal full widths indicate the presence of cancer;
 e) for measured full widths classified as abnormal full widths, measuring the triglyceride levels of the sample;
 f) classifying the triglyceride level so measured into the category of normal levels or above normal levels;
 g) for samples having above normal levels of triglycerides, subjecting the sample to a second nuclear magnetic resonance spectroscopy to generate an NMR spectrum;
 h) selecting a resonance line for lipoproteins in the region in said spectrum;
 i) measuring the intensity of said resonance line; and
 j) classifying the NMR spectrum into a category of normal spectrum or into a category of abnormal spectrum as compared to a predetermined standard for which abnormal spectrum indicate the presence of cancer.

26. The method of claim 25 wherein the non-water component is a lipid.

27. The method of claim 25 wherein the sample is blood plasma, spinal fluid or bone marrow plasma, and wherein said selected resonance line is from the allylic and/or bis-allylic groups of the lipoprotein lipids.

28. The method of claim 25 wherein the ratio of the intensities of the peaks of the second proton NMR spectrum at 2.0 and 2.8 ppm is indicative of the presence of cancer.

29. A method of diagnosing the presence of cancer in a living patient, comprising the following steps:
 a) subjecting a sample from a patient to be tested to nuclear magnetic resonance spectroscopy to generate an NMR spectrum;
 b) selecting a plurality of NMR resonance lines in said spectrum from a non-water component of said sample;
 c) measuring the full width at half-height of each of said lines;
 d) deriving from all full widths so measured a composite linewidth;
 e) classifying the composite linewidth so derived into a category of normal composite linewidths or into a category of abnormal composite linewidths as compared to a predetermined standard for which abnormal composite linewidths indicate the presence of cancer;
 f) for measured composite linewidths classified as abnormal composite linewidths, measuring the triglyceride levels of the sample;
 g) classifying the triglyceride level so measured into the category of normal levels or above normal levels;
 h) for samples having above normal levels of triglycerides, subjecting the sample to a second nuclear magnetic resonance spectroscopy to generate an NMR spectrum;
 i) selecting a resonance line for lipoproteins in the region in said spectrum;
 j) measuring the area of said resonance line; and
 k) classifying the NMR spectrum into a category of normal spectrum or into a category of abnormal spectrum as compared to a predetermined standard for which abnormal spectrum indicate the presence of cancer.

30. The method of claim 29 wherein the ratio of the areas of the peaks of the second proton NMR spectra at 2.0 and 2.8 ppm is indicative of the presence of cancer.

31. A method of diagnosing the presence of cancer in a living patient, comprising the following steps:
 a) subjecting a sample from a patient to be tested to nuclear magnetic resonance spectroscopy to generate an NMR spectrum;
 b) selecting a plurality of NMR resonance lines in said spectrum from a non-water component of said sample;

c) measuring the full width at half-height of each of said lines;

d) deriving from all full widths so measured a composite linewidth;

e) classifying the composite linewidth so derived into a category of normal composite linewidths or into a category of abnormal composite linewidths as compared to a predetermined standard for which abnormal composite linewidths indicate the presence of cancer;

f) for measured composite linewidths classified as abnormal composite linewidths, measuring the triglyceride levels of the sample;

g) classifying the triglyceride level so measured into the category of normal levels or above normal levels;

h) for samples having above normal levels of triglycerides, subjecting the sample to a second nuclear magnetic resonance spectroscopy to generate an NMR spectrum;

i) selecting a resonance line for lipoproteins in the region in said spectrum;

j) measuring the intensity of said resonance line; and k) classifying the NMR spectrum into a category of normal spectrum or into a category of abnormal spectrum as compared to a predetermined standard for which abnormal spectrum indicate the presence of cancer.

32. The method of claim 31 wherein the ratio of the intensities of the peaks of the second proton NMR spectra at 2.0 and 2.8 ppm is indicative of the presence of cancer.

33. A method of diagnosing the presence of cancer in a living patient, comprising the following steps:

a) subjecting a sample of blood plasma, bone marrow plasma or spinal fluid to proton nuclear magnetic resonance spectroscopy to generate an NMR spectrum from which the water signal has been suppressed;

b) selecting the resonance lines of the methyl and methylene groups of the lipoprotein lipids in said spectrum;

c) measuring the full width at half-height of each of said resonance lines;

d) computing an average width from the full widths so measured;

e) classifying the average width computed into the category of normal average widths or into the category of abnormal average widths as compared to a predetermined standard for which abnormal average widths indicate the presence of cancer;

f) for measured composite linewidths classified as abnormal composite linewidths, measuring the triglyceride levels of the blood component sample;

g) classifying the triglyceride level so measured into the category of normal levels or above normal levels;

h) for samples having above normal levels of triglycerides, subjecting the sample to a second nuclear magnetic resonance spectroscopy to generate an NMR spectrum;

i) selecting a resonance line for lipoproteins in the region in said spectrum;

j) measuring the area of said resonance line; and k) classifying the NMR spectrum into a category of normal spectrum or into a Category of abnormal spectrum as compared to a predetermined standard for which abnormal spectrum indicate the presence of cancer.

34. The method of claim 33 wherein the ratio of the areas of the peaks of the second proton NMR spectra at 2.0 and 2.8 ppm is indicative of the presence of cancer.

35. A method of diagnosing the presence of cancer in a living patient, comprising the following steps:

a) subjecting a sample of blood plasma, bone marrow plasma or spinal fluid to proton nuclear magnetic resonance spectroscopy to generate an NMR spectrum from which the water signal has been suppressed;

b) selecting the resonance lines of the methyl and methylene groups of the lipoprotein lipids in said spectrum;

c) measuring the full width at half-height of each of said resonance lines;

d) computing an average width from the full widths so measured;

e) classifying the average width computed into the category of normal average widths or into the category of abnormal average widths as compared to a predetermined standard for which abnormal average widths indicate the presence of cancer;

f) for measured composite linewidths classified as abnormal composite linewidths, measuring the triglyceride levels of the blood component sample;

g) classifying the triglyceride level so measured into the category of normal levels or above normal levels;

h) for samples having above normal levels of triglycerides, subjecting the sample to a second nuclear magnetic resonance spectroscopy to generate an NMR spectrum;

i) selecting a resonance line for lipoproteins in the region in said spectrum;

j) measuring the intensity of said resonance line; and k) classifying the NMR spectrum into a category of normal spectrum or into a category of abnormal spectrum as compared to a predetermined standard for which abnormal spectrum indicate the presence of cancer.

36. The method of claim 35 wherein the ratio of the intensities of the peaks of the second proton NMR spectra at 2.0 and 2.8 ppm is indicative of the presence of cancer.

37. A method for detecting cancer comprising:

a) establishing a value for at least one NMR parameter for nuclei of at least one moiety associated with a constituent, other than water, of a lipid-containing bodily fluid of cancer-free subjects;

b) exposing the same type bodily fluid of a subject to be diagnosed for cancer to a magnetic field and radio-frequency energy to generate a nuclear magnetic resonance spectrum;

c) processing the nuclear magnetic resonance spectrum to obtain a value for said parameter of said moiety nuclei;

d) comparing the value established for said parameter in (a) with the value obtained in (c);

e) classifying the value so established into either a category of normal or into a category of abnormal as compared to a predetermined standard for which abnormal value widths indicate the presence of cancer;

f) for measured value widths classified as abnormal value widths, measuring the triglyceride levels of the bodily fluid;

g) classifying the triglyceride level so measured into the category of normal levels or above normal levels;

h) for bodily fluids samples having above normal levels of triglycerides, subjecting the bodily fluid to a second nuclear magnetic resonance spectroscopy to generate an NMR spectrum;

i) selecting a resonance line for lipoproteins in the region in said spectrum;

j) measuring the area said resonance line; and k) classifying the NMR spectrum into the category of normal spectrum or into the category of abnormal spectrum as compared to a predetermined standard for which abnormal spectrum indicate the presence of cancer.

38. A method in accordance with claim 37 wherein said lipid-containing bodily fluid is blood, blood serum or blood plasma.

39. A method in accordance with claim 37, wherein a sample of said bodily fluid is removed from the subject to be diagnosed and steps (b and (c) are conducted in vitro.

40. A method in accordance with claim 37 wherein said nuclei are protons and wherein said moiety in step (a) is selected from the group consisting of methyl and methylene.

41. A method in accordance with claim 40 wherein said methyl and methylene are associated with lipoprotein.

42. A method in accordance with claim 41 wherein said proton NMR parameter is an average value derived from the resonance lines of methyl and methylene protons.

43. A method in accordance with claim 40 additionally comprising suppressing the NMR resonance signal of water.

44. A method in accordance with claim 37 wherein the parameter in step (a) is the average value of the full widths at half-height of the methyl and methylene proton resonances.

45. A method in accordance with claim 37 wherein the parameter in step (a) is the full width a half-height of the NMR resonance line of said moiety nuclei.

46. A method in accordance with claim 37 wherein the parameter in step (a) is the apparent spin-spin relaxation time $T_2^*$.

47. A method in accordance with claim 37 additionally comprising suppressing the NMR resonance signal of water.

48. The method of claim 37 wherein the ratio of the area of the peaks of the second proton NMR spectrum at 2.0 and 2.8 ppm is indicative of the presence of cancer.

49. A method for detecting cancer comprising:
a) establishing a value for at least one NMR parameter for nuclei of at least one moiety associated with a constituent, other than water, of a lipid-containing bodily fluid of cancer-free subjects;

b) exposing the same type bodily fluid of a subject to be diagnosed for cancer to a magnetic field and radio-frequency energy to generate a nuclear magnetic resonance spectrum;

c) processing the nuclear magnetic resonance spectrum to obtain a value for said parameter of said moiety nuclei;

d) comparing the value established for said parameter in (a) with the value obtained in (c);

e) classifying the value so established into either a category of normal or into a category of abnormal as compared to a predetermined standard for which abnormal value widths indicate the presence of cancer;

f) for measured value widths classified as abnormal value widths, measuring the triglyceride levels of the bodily fluid;

g) classifying the triglyceride level so measured into the category of normal levels or above normal levels;

h) for bodily fluids samples having above normal levels of triglycerides, subjecting the bodily fluid to a second nuclear magnetic resonance spectroscopy to generate an NMR spectrum;

i) selecting a resonance line for lipoproteins in the region in said spectrum;

j) measuring the intensity of said resonance line; and k) classifying the NMR spectrum into the category of normal spectrum or into the category of abnormal spectrum as compared to a predetermined standard for which abnormal spectrum indicate the presence of cancer.

50. A method in accordance with claim 49 wherein said lipid-containing bodily fluid is blood, blood serum or blood plasma.

51. A method in accordance with claim 49, wherein a sample of said bodily fluid is removed from the subject to be diagnosed and steps (b and (c) are conducted in vitro.

52. A method in accordance with claim 49 wherein said nuclei are protons and wherein said moiety in step (a) is selected from the group consisting of methyl and methylene.

53. A method in accordance with claim 49 wherein said methyl and methylene are associated with lipoprotein.

54. A method in accordance with claim 50 wherein said proton NMR parameter is an average value derived from the resonance lines of methyl and methylene protons.

55. A method in accordance with claim 49 wherein the parameter in step (a) is the average value of the full widths at half-height of the methyl and methylene proton resonances.

56. A method in accordance with claim 49 wherein the parameter in step (a) is the full width at half-height of the NMR resonance line of said moiety nuclei.

57. A method in accordance with claim 49 wherein the parameter in step (a) is the apparent spin-spin relaxation time $T_2^*$.

58. A method in accordance with claim 49 additionally comprising suppressing the NMR resonance signal of water.

59. The method of claim 49 wherein the ratio of the intensities of the peaks of the second proton resonance spectra at 2.0 and 2.8 ppm is indicative of the presence of cancer.

* * * * *